United States Patent [19]

Marfat

[11] Patent Number: 4,551,452

[45] Date of Patent: Nov. 5, 1985

[54] ANTI-INFLAMMATORY 2-METHYL-2H-1,2-BENZO-(OR -THIENO-)THIAZINE-3-CARBOXAMIDE 1,1-DIOXIDE DERIVATIVES, COMPOSITIONS, AND METHOD OF USE THEREFOR

[75] Inventor: Anthony Marfat, Groton, Conn.

[73] Assignee: Pfizer Inc., New York, N.Y.

[21] Appl. No.: 606,113

[22] Filed: May 2, 1984

Related U.S. Application Data

[63] Continuation-in-part of Ser. No. 563,902, Dec. 21, 1983, abandoned.

[51] Int. Cl.$^4$ .................. C07D 513/04; C07D 279/02; A61K 31/54
[52] U.S. Cl. .................................... 514/222; 514/225; 544/48; 544/49
[58] Field of Search .................... 544/48, 49; 424/246; 514/222, 225

[56] References Cited

U.S. PATENT DOCUMENTS

| | | |
|---|---|---|
| 3,591,584 | 7/1971 | Lombardino ........................ 260/243 |
| 3,787,324 | 1/1974 | Zinnes ............................... 260/243 R |
| 3,822,258 | 7/1974 | Zinnes et al. .................... 260/243 R |
| 3,892,740 | 7/1975 | Lombardino .................... 260/243 R |
| 4,180,662 | 12/1979 | Pfister et al. ........................... 544/48 |
| 4,309,427 | 1/1982 | Lombardino ....................... 424/246 |

FOREIGN PATENT DOCUMENTS

| | | |
|---|---|---|
| 895712 | 5/1983 | Belgium ................................ 544/49 |
| 85866 | 1/1983 | European Pat. Off. .............. 544/49 |

*Primary Examiner*—Henry R. Jiles
*Assistant Examiner*—J. G. Mullins
*Attorney, Agent, or Firm*—Charles J. Knuth; Albert E. Frost; Robert K. Blackwood

[57] ABSTRACT

Certain enol ether derivatives of oxicams (1,1-dioxides of N-heteroaryl-4-hydroxy-2-methyl-2H-1,2-benzothiazine-3-carboxamides and N-heteroaryl-4-hydroxy-2-methyl-2H-thieno[2,3-e]-1,2-thiazine-3-carboxamides) are useful as prodrugs of these antiinflammatory compounds.

28 Claims, No Drawings

ANTI-INFLAMMATORY 2-METHYL-2H-1,2-BENZO-(OR -THIENO-)THIAZINE-3-CARBOXAMIDE 1,1-DIOXIDE DERIVATIVES, COMPOSITIONS, AND METHOD OF USE THEREFOR

CROSS REFERENCE TO RELATED APPLICATION

This application is a continuation-in-part of copending U.S. patent application Ser. No. 563,902, filed Dec. 21, 1983 now abandoned.

BACKGROUND OF THE INVENTION

The present invention is concerned with enol ether derivatives of oxicams (1,1-dioxides of N-heteroaryl-4-hydroxy-2-methyl-2H-1,2-benzothiazine-3-carboxamides and N-heteroaryl-4-hydroxy-2-methyl-2H-thieno[2,3-e]-1,2-thiazine-3-carboxamides). These ethers are valuable as so-called prodrugs of these nonsteroidal antiinflammatory agents, known generically as oxicams.

The oxicams (including enol esters) and their utility as antiinflammatory agents are disclosed in U.S. Pat. Nos. 3,591,584; 3,787,324; 3,822,258; 4,180,662; and 4,309,427; Belgian Pat. No. 895,712; and European patent application No. 85,866. Prior described enol ethers of oxicams (U.S. Pat. No. 3,892,740) do not exhibit present antiinflammatory activity.

SUMMARY OF THE INVENTION

The present invention encompasses antiinflammatory prodrug enol ethers of the formula

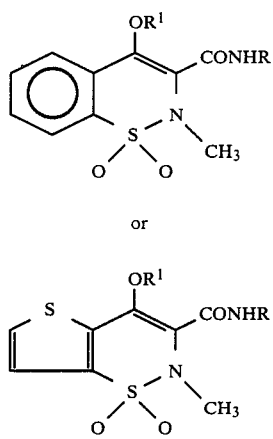

wherein R is

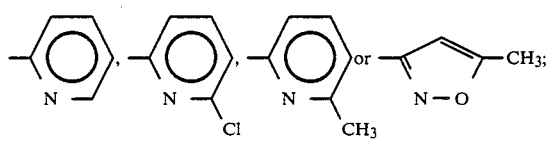

and $R^1$ is

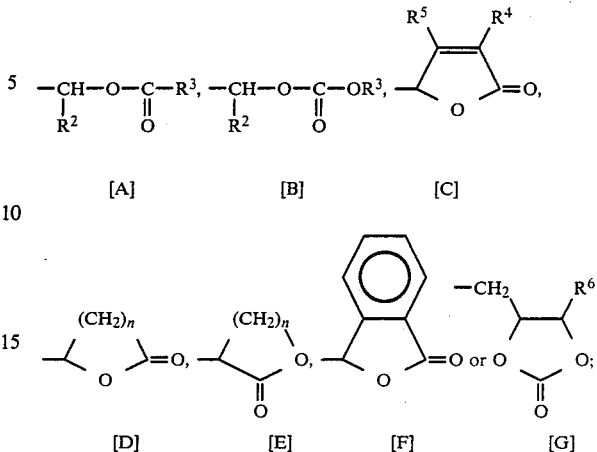

$n$ is 2, 3 or 4;

$R^2$ is hydrogen, methyl or phenyl;

$R^4$ and $R^5$ are each independently hydrogen or $(C_1-C_3)$alkyl;

$R^3$ is $(C_1-C_{10})$alkyl, $(C_3-C_7)$cycloalkyl, phenyl or benzyl, each optionally substituted by $OR^6$ or $OCOR^6$, and $R^6$ is $(C_1-C_3)$alkyl.

The preferred compounds are piroxicam derivatives, of the formula (I) with R as 2-pyridyl, particularly with $R^1$ as 1-(propionyloxy)ethyl (radical [A], $R^2=CH_3$, $R^3=C_2H_5$); 1-(cyclopropylcarbonyloxy)ethyl (radical [A], $R^2=CH_3$, $R^3=$cyclopropyl); 1-(benzoyloxy)ethyl (radical [A], $R^2=CH_3$, $R^3=C_6H_5$); 1-(2-methyl-2-methoxycarbonylpropionyloxy)methyl (radical [A], $R^2=H$, $R^3=C(CH_3)_2COOCH_3$); 1-(ethoxycarbonyloxy)ethyl (radical [B], $R^2=CH_3$, $R^3=C_2H_5$); 1-(benzyloxycarbonyloxy)ethyl (radical [B], $R^2=CH_3$, $R^3=CH_2C_6H_5$); 1-(cyclohexyloxycarbonyloxy)ethyl (radical [B], $R^2CH_3$, $R^3=$cyclohexyl); 1-(decyloxycarbonyloxy)ethyl (radical [B], $R^2=CH_3$, $R^3=$n-$C_{10}H_{21}$); 2-(gamma-buryrolactonyl) (radical [E], n=2); 5-(2-oxo-2,5-dihydrofuryl) (radical [C], $R^4=R^5=H$); 1-(4-methyl-2-oxo-1,3-dioxol-5-yl)methyl (radical [G], $R^6=CH_3$), or 3-phthalidyl (radical [F]). Other preferred compounds have $R^1$ as 1-(ethoxycarbonyloxy)ethyl, having the formula (II) with R as 2-pyridyl, or having the formula (I) having R as 6-methyl-2-pyridyl, 6-chloro-2-pyridyl or 5-methyl-3-isoxazolyl; or have $R^1$ as 1-(acetoxy)ethyl or 1-(propionyloxy)ethyl having the formula (I) with R as 6-methyl-2-pyridyl.

The term "prodrug" refers to compounds which are drug precursors which, following administration, release the drug in vivo via some metabolic process such as hydrolysis.

The present invention also encompasses pharmaceutical compositions suitable for administration to a mammal which comprise an antiinflammatory amount of a compound of the formula (I) or (II), and a method of treating inflammatory conditions in a mammal which comprises treatment with an antiinflammatory amount of a compound of the formula (I) or (II). While all of the usual routes of administration, including topical, are useful with the instant compounds, the preferred route of administration is oral. After gastrointestinal absorption, the present compounds are hydrolyzed in vivo to the present antiinflammatory oxicam. Since the present compounds are non-acidic, exposure of the gastrointestinal tract to the acidic oxicam compound is thereby minimized.

DETAILED DESCRIPTION OF THE INVENTION

The compounds of the present invention, of the above formula (I) or (II), are readily and generally prepared by a nucleophilic displacement reaction such as follows:

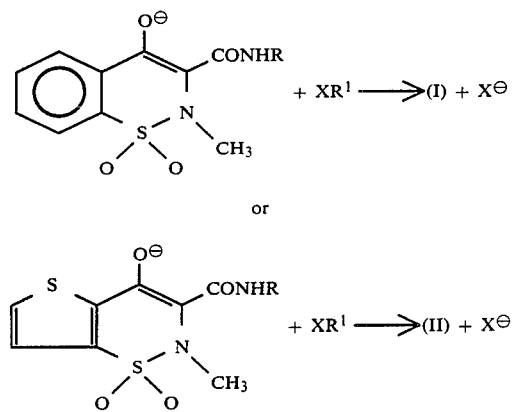

where R and $R^1$ are as defined above and X is a nucleophilically displaceable group such as halo (Cl, Br or I) or sulfonate ester (e.g., mesylate or tosylate).

The required oxicam salt can be preformed, or more conveniently, formed in situ by use of at least one equivalent of a base. The reaction is carried out in a reaction-inert solvent, preferably one which is essentially anhydrous. A particularly convenient reaction system employs excess potassium carbonate as base in acetone as solvent. The preferred value of X is chloro or bromo, with up to three or more equivalents of anhydrous sodium iodide added, if desired, to enhance the rate of reaction. Excess of the reagent $R^1X$ is not critical to the reaction, but such an excess will generally be used in order to force the reaction to completion in a shorter period of time. The rate of reaction will also depend greatly on the value of X (e.g., I<Br<Cl) and on the nature of the group $R^1$

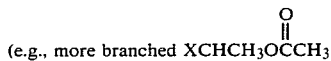

will react more slowly than

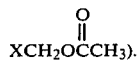

The reaction temperature is not critical, a temperature in the range of 50°–100° C. being generally satisfactory. With $K_2CO_3$ as base and acetone as solvent, the reflux temperature of acetone is particularly convenient. The reactions are conveniently followed by thin-layer chromatography, thereby determining reaction times sufficient to provide complete reaction and at the same time avoiding unnecessary heating costs and excessive reaction times, which can increase the level of by-products and reduce yields.

The oxicams required as starting materials are available by methods well known in the art (see, for example, the references to oxicams cited above). The required reagents $R^1X$ are available commercially, by known methods, or by methods detailed in the Preparations section below.

The present oxicam derivatives (I) and (II) are also evaluated for their antiinflammatory activity according to known methods such as the rat foot edema test, rat adjuvant-induced arthritis test, or phenylbenzoquinone-induced writhing test in mice, as previously used in the evaluation of the parent oxicams and described in references cited above and elsewhere in the literature.

On a molar basis, the present oxicam prodrugs are generally dosed at the same level and frequency as the known oxicams from which they are derived. However, the non-acidic nature of the present compounds will generally permit higher tolerated oral doses, when such higher dosage is required in the control of inflammation.

The present oxicam prodrugs are also formulated in the same manner, and administered by the same routes as the known oxicams, as described in the above cited references. The preferred route of administration is oral, thus taking particular advantage of the non-acidic nature of the present compounds.

The present invention is illustrated by the following examples, but is not limited to the specific details of these examples.

EXAMPLE 1

4-[5-(2-Oxo-2,5-dihydrofuryl)oxy]-2-methyl-N-(2-pyridyl)-2H-1,2-benzothiazine-3-carboxamide 1,1-Dioxide To a round bottomed flask equipped with a reflux condenser and stirring bar were added 2-methyl-N-(2-pyridyl)-4-hydroxy-2H-1,2-benzothiazine-3-carboxamide 1,1-dioxide (piroxicam; 3.00 g, 9.06 mmol), potassium carbonate (2.50 g, 18.1 mmol), 2-oxo-5-bromo-2,5-dihydrofuran (Elming et al., Acta. Chem. Scand. 6, p. 566, 1952; 1.77 g, 10.8 mmol), and acetone (45 mL). The heterogenous reaction mixture was heated to reflux under a nitrogen atmosphere. After 10 minutes the dark brown mixture was removed from heat. The acetone was removed in vacuo leaving a brown residue which was treated with water (200 mL) and methylene chloride (200 mL). The organic layer was separated and the aqueous layer extracted with additional methylene chloride (200 mL). The combined organic extracts were washed with water (200 mL), brine (200 mL), dried ($Na_2SO_4$) and concentrated in vacuo to a brown oil. Column chromatography on silica (2:8 ethyl acetate:methylene chloride) afforded 2.6 g (6.29 mmol, 69.4%) of a yellow solid: TLC (2:8 ethyl acetate:methylene chloride) $R_f$ 0.42. Recrystallization from toluene/hexane gave an oil which crystallized upon refrigeration to yield 520 mg of pale yellow crystals: mp 142°–143° C.; IR (KBr) 1778, 1689 cm$^{-1}$; $^1$H NMR (CDCl$_3$) delta 3.10 (s, 3H), 6.28–6.37 (m, 1H), 6.45–6.52 (m, 1H), 7.10–7.19 (m, 1H), 7.59–7.95 (m, 5H), 8.02–8.11 (m, 1H), 8.26–8.41 (m, 2H), 9.20 (br s, 1H); precise mass calcd. for $C_{19}H_{16}N_3O_6S$ m/e (P$^+$+H) 414.0767, found 414.0794.

Anal. Calcd. for $C_{19}H_{15}N_3O_6S$: C, 55.20; H, 3.66; N, 10.16.

Found: C, 55.04; H, 3.73; N, 9.91.

EXAMPLE 2

4-[2-gamma-Butyrolacetonyl)oxy]-2-methyl-N-(2-pyridyl)-2H-1,2-benzothiazine-3-carboxamide 1,1-Dioxide To a round bottomed flask equipped with a reflux condenser and stirring bar were added piroxicam (9.00 g, 27.2 mmol), potassium carbonate (7.50 g, 54.3 mmol), alpha-bromo-gamma-butyrolactone (13.45 g, 81.5 mmol), and acetone (60 mL). The heterogeneous mixture was heated to reflux under a nitrogen atmosphere. After 20 hours TLC (1:4 ethyl acetate:methylene chloride) indicated complete consumption of starting material and formation of product. The reaction mixture was concentrated in vacuo at room temperature. The residue was treated with water (500 mL) and extracted twice with methylene chloride (500 mL). The combined organic extracts were washed with brine (300 mL), dried over sodium sulfate, and concentrated in vacuo to a brown oil. Column chromatography on silica (1:3 ethyl acetate:methylene chloride) afforded 5.85 g (51.8%) of a light brown solid which was recrystallized from isopropyl alcohol to yield off-white crystals (3.36 g, 29.8%): mp 181°–183° C.; IR (KBr) 1785, 1690 cm$^{-1}$; $^1$H NMR (CDCl$_3$) delta 2.54 (m, 2H), 3.12 (s, 3H), 4.20 (dd, J=7.9 Hz, J=2.0 Hz, 1H), 4.47 (m, 1H), 4.81 (t, J=6.0 Hz, 1H), 7.13 (m, 1H), 7.78 (m, 3H), 7.94 (m, 1H), 8.17 (m, 1H), 8.34 (m, 1H), 9.34 (br s, 1H); mass spectrum: m/e=330 (P$^+$−C$_4$H$_5$O$_2$).

Anal. calcd. for C$_{19}$H$_{17}$N$_3$O$_6$S: C, 54.93; H, 4.12; N, 10.12.

Found: C, 54.64; H, 4.08; N, 10.21.

By the same method, alpha-bromo-delta-valerolactone and piroxicam are converted to 4-[2-(delta-valerolactonyl)oxy]-2-methyl-N-(2-pyridyl)-2H-1,2-benzothiazine-3-carboxamide 1,1-dioxide; and delta-bromodelta-butyrolactone and piroxicam are converted to 4-[4-(delta-butyrolactonyl)oxy]-2-methyl-N-(2-pyridyl)-2H-1,2-benzothiazine-3-carboxamide 1,1-dioxide.

EXAMPLE 3

4-[(4-Methyl-2-oxo-1,3-dioxol-5-yl)methyloxy]-2-methyl-N-(2-pyridyl)-2H-1,2-benzothiazine-3-carboxamide 1,1-Dioxide To a round bottomed flask equipped with a reflux condenser and stirring bar was added piroxicam (5.00 g, 15.1 mmol), potassium carbonate (4.20 g, 30.2 mmol), 5-bromomethyl-4-methyl-2-oxo-1,3-dioxole (prepared according to European patent application No. 39,477; 4.37 g, 22.6 mmol) and acetone (60 ml). The heterogenous reaction mixture was heated to reflux under a nitrogen atmosphere for 20 minutes, at which time no piroxicam was visible by TLC (1:4 ethyl acetate:methylene chloride, visualization by UV light). The acetone was removed in vacuo leaving a brown residue which was treated with water (200 mL) and methylene chloride (200 mL). The organic layer was separated and the aqueous layer extracted with additional methylene chloride (200 mL). The combined organic extracts were washed with water (200 mL), brine (200 mL), dried (Na$_2$SO$_4$) and concentrated in vacuo to a brown oil. Column chromatography on silica gel, eluting with 1:4 ethyl acetate:methylene chloride and collecting all fractions containing the R$_f$ 0.30 spot, afforded a yellow solid. The latter was recrystallized from hot toluene to yield 3.08 g white crystals (6.95 mmol, 46.0%): mp 157°–158° C.; IR (KBr) 1836, 1824, 1671 cm$^{-1}$; $^1$H NMR (CDCl$_3$) delta 1.95 (s, 3H), 3.13 (s, 3H), 4.79 (s, 2H), 7.10–7.21 (m, 1H), 7.70–7.99, (m, 5H), 8.27–8.42, (m, 2H), 9.45 (br s, 1H); Precise mass calcd for C$_{15}$H$_{12}$N$_3$O$_4$S m/e 330.0553, found 330.0567, for C$_5$H$_5$O$_3$ m/e 113.0243, found 113.0244.

Anal. Calcd. for C$_{20}$H$_{17}$N$_3$O$_7$S: C, 54.17; H, 3.86; N, 9.48.

Found C, 54.52; H, 3.93; N, 9.41.

EXAMPLE 4

4-(3-Phthalidyloxy)-2-methyl-N-(2-pyridyl)-2H-1,2-benzothiazine-3-carboxamide 1,1-Dioxide To a round bottomed flask equipped with a reflux condenser and a stirring bar were added piroxicam (3.00 g, 9.1 mmol), potassium carbonate (2.50 g, 18.2 mmol), 3-bromophthalide (prepared according to U.K. Pat. No. 1,364,672; 2.51 g, 11.8 mmol) and acetone (45 mL). The heterogenous reaction mixture was heated to reflux under a nitrogen atmosphere. After 0.5 hour the solvent was removed in vacuo leaving a brown residue which was treated with water (200 mL) and methylene chloride (200 mL). The organic layer was separated and the aqueous layer extracted with additional methylene chloride (200 mL). The combined organic extracts were washed with water (200 mL), brine (200 mL), dried (Na$_2$SO$_4$) and concentrated in vacuo to a brown oil. Column chromatography on silica (1:9 ethyl acetate:methylene chloride) afforded a white foam which, when dissolved in hot toluene, precipitated within a few seconds as pure white crystals: 3.42 g (7.38 mmol, 81.5%); mp 151°–152° C.; IR (KBr) 1785, 1688 cm$^{-1}$; $^1$H NMR (CDCl$_3$) delta 3.13 (s, 3H), 6.97 (s, 1H), 7.07–7.35 (m, 1H), 7.58–8.18 (m, 9H), 8.30–8.44 (m, 2H), 9.18 (br s, 1H): precise mass calcd for C$_{23}$H$_{17}$N$_3$O$_6$S m/e 463.0855, found 463.0871.

Anal. Calcd. for C$_{23}$H$_{17}$N$_3$O$_6$S: C, 59.61; H, 3.70; N, 9.01.

Found: C, 59.75; H, 3.76; N, 8.73.

EXAMPLE 5

4-[1-(Propionyloxy)ethoxy]-2-methyl-N-(2-pyridyl)-2H-1,2-benzothiazine-3-carboxamide 1,1-Dioxide To a round bottomed flask equipped with a reflux condenser and stirring bar were added piroxicam (2.00 g, 6.0 mmol), potassium carbonate (1.67 g, 12.1 mmol), alpha-chloroethyl propionate (2.50 g, 18.1 mmol) and acetone (30 mL). The heterogenous reaction mixture was heated to reflux under a nitrogen atmosphere. After 24 hours, anhydrous sodium iodide (4.52 g, 30.2 mmol) was added and reflux continued an additional 0.5 hour. The acetone was removed in vacuo leaving a brown residue which was treated with water (200 mL) and methylene chloride (200 mL). The combined organic extracts were washed with water (200 mL), brine (200 mL), dried (Na$_2$SO$_4$) and concentrated in vacuo to a brown oil. Column chromatography on silica (1:9 ethyl acetate:methylene chloride) afforded 1.17 g of a yellow solid (2.7 mmol. 44.9%) which was crystallized from isopropyl alcohol to yield 998 mg pure white crystals: mp 156°–158° C.; IR (KBr) 1748, 1677 cm$^{-1}$; $^1$H NMR (CDCl$_3$) delta 0.98 (t, J=7 Hz, 3H), 1.73 (d, J=6 Hz, 3H), 2.10–2.39 (m, 2H), 3.13 (s, 3H), 6.41 (q, J=6 Hz, 1H), 7.07–7.17 (m, 1H), 7.63–7.95 (m, 5H), 8.31–8.41 (m, 2H), 9.57 (br s, 1H); precise mass calcd for C$_{20}$H$_{21}$N$_3$O$_6$S m/e 431.1157, found 431.1092.

Anal. Calcd. for $C_{20}H_{21}N_3O_6S$: C, 55.68; H, 4.91; N, 9.47.
Found: C, 55.91; H, 5.04; N, 9.77.

EXAMPLE 6

4-[1-Benzyloxycarbonyloxy)ethoxy]-2-methyl-N-(2-pyridyl)-2H-1,2-benzothiazine-3-carboxamide 1,1-Dioxide To a round bottomed flask equipped with a reflux condenser and stirring bar were added piroxicam (3.00 g, 9.1 mmol), potassium carbonate (2.50 g, 18.1 mmol), alpha-chloroethyl benzyl carbonate (5.56 g, 27.2 mmol) and acetone (45 mL). The heterogenous reaction mixture was heated to reflux under a nitrogen atmosphere. After 20 hours sodium iodide (4.52 g, 30.2 mmol) was added and reflux continued an additional 8 hours. Chromatographed title product was isolated according to the preceding Example, affording 3.24 g white foam (6.4 mmol, 70.2%) which crystallized from toluene/hexane: mp 120°–122° C.; IR (KBr) 1761, 1680 cm$^{-1}$; $^1$H NMR (CDCl$_3$) delta 1.75 (d, J=6 Hz, 3H), 3.12 (s, 3H), 5.02 (d, J=1 Hz, 2H), 6.41 (q, J=6 Hz, 1H), 7.03–7.14 (m, 1H), 7.14–7.30 (m, 5H), 7.62–7.97 (m, 5H), 8.25–8.38 (m, 2H), 9.38 (br s, 1H); precise mass calcd for $C_{25}H_{23}N_3O_7S$ m/e 509.1257, found 509.1163.

Anal. Calcd. for $C_{25}H_{23}N_3O_7S$: C, 58.93; H, 4.55; N, 8.25.
Found: C, 59.01; H, 4.53; N, 8.32.

EXAMPLE 7

4-[1-(Propoxycarbonyloxy)ethoxy]-2-methyl-N-(2-pyridyl)-2H-1,2-benzothiazine-3-carboxamide 1,1-Dioxide By the procedure of Example 6, piroxicam (3.00 g, 9.1 mmol) and alpha-chloroethyl propyl carbonate (4.52 g, 27.2 mmol) were converted to chromatographed title product, 3.47 g pale yellow foam (7.5 mmol, 83.0%) which gave 3.00 g white crystals from isopropyl alcohol: mp 150°–151° C.; IR (KBr) 1760, 1678 cm$^{-1}$; $^1$H NMR (CDCl$_3$) delta 0.84 (t, J=7 Hz, 3H), 1.46–1.65 (m, 2H), 1.75 (d, J=6 Hz, 3H), 3.11 (s, 3H), 3.97 (t, J=7 Hz, 2H), 6.35 (q, J=6 Hz, 1H), 7.04–7.16 (m, 1H), 7.62–7.97 (m, 5H), 8.30–8.41 (m, 2H), 9.40 (br s, 1H): precise mass calcd for $C_{21}H_{23}N_3O_7S$ m/e 461.1264, found 461.1260.

Anal. Calcd. for $C_{21}H_{23}N_3O_7S$: C, 54.66; H, 5.02; N, 9.11.
Found: C, 55.00; H, 5.13; N, 9.19.

EXAMPLE 8

4-[1-(Cyclohexyloxycarbonyloxy)ethoxy]-2-methyl-N-(2-pyridyl)-2H-1,2-benzothiazine-3-carboxamide 1,1-Dioxide By the procedure of Example 6, piroxicam (3.00 g, 9.1 mmol) and alpha-chloroethyl cyclohexyl carbonate (5.37 g, 26.1 mmol) were converted to chromatographed title product, 3.85 g pale yellow foam (7.7 mmol, 84.7%) which gave 2.45 g white crystals from toluene/hexane: mp 142°–144° C.; IR (KBr) 1749, 1682 cm$^{-1}$; $^1$H NMR (CDCl$_3$) delta 0.99–1.93 (br m, 10 H), 1.76 (d, J=6 Hz, 3H), 3.11 (s, 3H), 4.40–4.58 (br m, 1H), 6.36 (q, J=6 Hz, 1H), 7.06–7.18 (m, 1H), 7.62–7.97 (m, 5H), 8.32–8.43 (m, 2H), 9.40 (br s, 1H); precise mass calcd for $C_{24}H_{27}N_3O_7S$ m/e 501.1576, found 501.1613.

Anal. Calcd. for $C_{24}H_{27}N_3O_7S$: C, 57.47; H, 5.43; N, 8.38.
Found: C, 57.37; H, 5.38; N, 8.27.

EXAMPLE 9

4-[1-(Decyloxycarbonyloxy)ethoxy]-2-methyl-N-(2-pyridyl)-2H-1,2-benzothiazine-3-carboxamide 1,1-Dioxide By the procedure of Example 6, piroxicam (3.00 g, 9.1 mmol) and alpha-chloroethyl decyl carbonate (4.79 g, 18.1 mmol) were converted to chromatographed title product, 4.46 g white foam (8.0 mmol, 88.0%) which gave white crystals from isopropyl alcohol: mp 84°–86° C.: IR (KBr) 1764, 1679 cm$^{-1}$; $^1$H NMR (CDCl$_3$) delta 0.89 (t, J=7 Hz, 3H), 1.09–1.41 (m, 14H), 1.41–1.60 (br m, 2H), 1.75 (d, J=6 Hz, 3H), 3.11 (s, 3H), 4.00 (t, J=7 Hz, 2H), 6.36 (q, J=6 Hz, 1H), 7.07–7.17 (m, 1H), 7.63–7.96 (m, 5H), 8.30–8.40 (m, 2H), 9.40 (br s, 1H); precise mass calcd for $C_{28}H_{37}N_3O_7S$ m/e 559.2352, found 559.2346.

Anal. Calcd for $C_{28}H_{37}N_3O_7S$: C, 60.09; H, 6.66; N, 7.51. Found: C, 60.10; H, 6.67; N, 7.49.

EXAMPLE 10

4-[1-(Isopropoxycarbonyloxy)ethoxy]-2-methyl-N-(2-pyridyl)-2H-1,2-benzothiazine-3-carboxamide 1,1-Dioxide To a round bottom flask equipped with a reflux condenser and a stirring bar were added piroxicam (3.00 g, 9.1 mmol), potassium carbonate (2.50 g, 18.1 mmol), alpha-chloroethyl isopropyl carbonate (3.02 g, 18.1 mmol) and acetone (45 mL). The heterogenous reaction mixture was heated to reflux under a nitrogen atmosphere. After 24 hours anhydrous sodium iodide (4.52 g, 30.2 mmol) was added and reflux continued an additional 72 hours. Chromatographed title product was isolated according to Example 5 affording 1.76 g white foam (3.8 mmol, 42.1%) which gave 1.27 g white crystals from isopropyl alcohol: mp 180°–181° C.; IR (KBr) 1761, 1675 cm$^{-1}$; $^1$H NMR (CDCl$_3$) delta 1.13 (d, J=7 Hz, 3H), 1.16 (d, J=7 Hz, 3H), 1.77 (d, J=6 Hz, 3H), 3.10 (s, 3H), 4.57–4.88 (m, 1H), 6.37 (q, J=6 Hz, 1H), 7.06–7.17 (m, 1H), 7.62–8.04 (m, 5H), 8.31–8.50 (m, 2H), 9.50 (br s, 1H); precise mass calcd for $C_{21}H_{23}N_3O_7S$ m/e 461.1257, found 461.1295.

Anal. Calcd for $C_{21}H_{23}N_3O_7S$: C, 54.66; H, 5.02; N, 9.11.
Found: C, 54.56; H, 5.02; N, 9.03.

EXAMPLE 11

4-[1-(Methoxycarbonyloxy)ethoxy]-2-methyl-N-(2-pyridyl)-2H-1,2-benzothiazine-3-carboxamide 1,1-Dioxide By the method of Example 6, using a reflux time of 1 hour prior to addition of a sodium iodide, piroxicam (2.00 g, 6.0 mmol) and alpha-chloroethyl methyl carbonate (2.50 g, 18.1 mmol) were converted to chromatographed title product as a yellow solid which was crystallized from isopropyl alcohol (660 mg, 1.5 mmol, 25.0%): mp 150°–151° C.; IR (KBr) 1757, 1677 cm$^{-1}$; $^1$H NMR (CDCl$_3$) delta 1.75 (d, J=6 Hz, 3H), 3.12 (s, 3H), 3.65 (s, 3H), 6.35 (q, J=6 Hz, 1H), 7.07–7.18 (m, 1H), 7.65–7.95 (m, 5H), 8.30–8.42 (m, 2H), 9.42 (br s, 1H); precise mass calcd for $C_{19}H_{19}N_3O_7S$ m/e 433.0944, found 433.1004.

Anal. calcd. for $C_{19}H_{19}N_3O_7S$: C, 52.29; H, 5.08; H, 9.63.
Found: C, 52.18; H, 4.41; N, 9.61.

EXAMPLE 12

4-[1-(Ethoxycarbonyloxy)ethoxy]-2-methyl-N-(6-methyl-2-pyridyl)-2H-1,2-benzothiazine-3-carboxamide 1,1-Dioxide By the procedure of Example 6, N-(6-methyl-2-pyridyl)-4-hydroxy-2-methyl-2H-1,2-benzothiazine-3-carboxamide 1,1-dioxide (1.0 g, 2.89 mmol) and alpha-chloroethyl ethyl carbonate (1.18 mL, 1.32 g, 8.67 mmol) were converted to crude title product as a light yellow oil which solidified upon standing at room temperature. Column chromatography on silica gel (8:2 methylene chloride:ethyl acetate) afforded 1.15 g (86.2%) light yellow solid which was recrystallized from isopropyl alcohol to give 1.1 g white crystals: mp 156°-157° C.; IR (KBr) 1765, 1680 cm$^{-1}$; $^1$H NMR (CDCl$_3$) delta 1.18 (t, J=7 Hz, 3H), 1.75 (d, J=6 Hz, 3H), 2.50 (s, 3H), 3.12 (s, 3H), 4.08 (q, J=7 Hz, 2H), 6.34 (q, J=6 Hz, 1H), 6.96 (d, J=6.5 Hz, 1H), 7.60-7.80 (m, 3H), 7.85-7.95 (m, 2H), 8.15 (d, J=8 Hz, 1H), 9.28 (br s, 1H); precise mass calcd for C$_{21}$H$_{23}$N$_3$SO$_7$ m/e 461.1257, found 461.1348.

Anal. Calcd. for C$_{21}$H$_{23}$N$_3$SO$_7$: C, 54.60; H, 5.02; N, 9.11.

Found: C, 54.35; H, 5.00; N, 9.04.

EXAMPLE 13

4-[1-(Ethoxycarbonyloxy)ethoxy]-2-methyl-N-(2-pyridyl)-2H-thieno[2,3-e]-1,2-thiazine-3-carboxamide 1,1-Dioxide By the procedure of the preceding Example, 4-hydroxy-2-methyl-N-(2-pyridyl)-2H-thieno[2,3-e]-1,2-thiazine-3-carboxamide 1,1-dioxide (0.15 g, 0.445 mmol) and alpha-chloroethyl ethyl carbonate (0.182 mL, 1.134 mmol) were converted to chromatographed title product, 0.19 g (94%) light yellow foamy solid. Crytstallization from toluene containing a small amount of hexane gave 0.15 g white crystalline product: mp 121°-123° C.; IR (KBr) 1775, 1683 cm$^{-1}$; $^1$H NMR (CDCl$_3$) 1.18 (t, J=7 Hz, 3H), 1.77 (d, J=6 Hz, 3H), 3.17 (s, 3H), 4.10 (q, J=7 Hz, 2H), 6.55 (q, J=6 Hz, 1H), 7.05-7.18 (m, 1H), 7.40 (d, J=6.7 Hz, 1H), 7.64 (d, J=6.7 Hz, 1H), 7.71-7.82 (m, 1H), 8.28-8.41 (m, 2H), 9.20 (br s, 1H); precise mass calcd for C$_{18}$H$_{17}$N$_3$O$_7$S$_2$ m/e 453.0664, found 453.0664.

Anal. Calcd. for C$_{18}$H$_{17}$N$_3$O$_7$S$_2$: C, 47.67; H, 4.22; N, 9.27.

Found: C, 47.65; H, 4.17; N, 9.21.

EXAMPLE 14

4-[1-(Ethoxycarbonyloxy)ethoxy]-2-methyl-N-(6-chloro-2-pyridyl)-2H-1,2-benzothiazine-3-carboxamide 1,1-Dioxide By the procedure of Example 6, N-(6-chloro-2-pyridyl)-4-hydroxy-2-methyl-2H-1,2-benzothiazine-3-carboxamide 1,1-dioxide (0.20 g, 0.547 mmol) and alpha-chloroethyl ethyl carbonate (0.225 mL, 0.25 g, 1.65 mmol) were converted to chromatographed title product, 0.22 g (83.6%) white crystalline product which was recrystallized from isopropyl alcohol to give 0.20 g white crystals: mp 161°-162.5° C.; IR (KBr) 1770, 1690 cm$^{-1}$; $^1$H NMR (CDCl$_3$) delta 1.19 (t, J=7 Hz, 3H), 1.76 (d, J=6 Hz, 3H), 3.08 (s, 3H), 4.09 (q, J=7 Hz, 2H), 6.34 (q, J=6 Hz, 1H), 7.16 (d, J=7.5 Hz, 1H), 7.66-7.91 (m, 3H), 7.81-7.96 (m, 2H), 8.30 (d, J=7.5 Hz, 1H), 9.39 (br s, 1H); precise mass calcd for C$_{20}$H$_{20}$N$_3$O$_7$S m/e 483.0681, found 483.0538.

Anal. Calcd. for C$_{20}$H$_{20}$N$_3$O$_7$SCl: C, 49.85; H, 4.18; N, 8.72.

Found: C, 49.72; H, 4.07; N, 8.73.

EXAMPLE 15

4-[1-(Hexyloxycarbonyloxy)ethoxy]-2-methyl-N-(2-pyridyl)-2H-1,2-benzothiazine-3-carboxamide 1,1-Dioxide By the procedure of Example 11, piroxicam (3.00 g, 9.1 mmol) and alpha-chloroethyl hexyl carbonate (2.85 g, 13.6 mmol) were converted to chromatographed title product, isolated as a yellow solid which was crystallized from isopropyl alcohol/hexane (280 mg, 0.5 mmol, 6.1%): mp 86°-87° C.; IR (KBr) 1764, 1678 cm$^{-1}$; $^1$H NMR (CCl$_3$) delta 0.87 (t, J=7 Hz, 3H), 1.05-1.39 (m, 6H), 1.41-1.60 (m, 2H), 1.75 (d, J=6 Hz, 3H), 3.10 (s, 3H), 4.00 (t, J=7 Hz, 2H), 6.36 (q, J=6 Hz, 1H), 7.06-7.17 (m, 1H), 7.63-7.86 (m, 5H), 8.31-8.42 (m, 2H), 9.39 (br s, 1H); precise mass calcd for C$_{24}$H$_{29}$N$_3$O$_7$S m/e 503.1737, found 503.1761.

Anal. Calcd. for C$_{24}$H$_{29}$N$_3$O$_7$S: C, 57.24; H, 5.80; N, 8.34.

Found: C, 57.32; H, 5.77; N, 8.39.

EXAMPLE 16

4-[1-(Ethoxycarbonyloxy)ethoxy]-2-methyl-N-(2-pyridyl)-2H-1,2-benzothiazine-3-carboxamide 1,1-Dioxide To a round bottomed flask equipped with a reflux condenser and stirring bar were added piroxicam (10.0 g, 30.2 mmol), potassium carbonate (8.35 g, 60.4 mmol), alpha-chloroethyl ethyl carbonate (12.35 mL, 13.81 g, 90.6 mmol) and acetone (350 mL). The heterogenous reaction mixture was heated to reflux under a nitrogen atmosphere. After 19 hours, anhydrous sodium iodide (22.6 g, 150.7 mmol) was added and reflux continued for an additional 5 hours. The acetone was removed in vacuo leaving a brown residue which was treated with water (250 mL) and methylene chloride (250 mL). The organic layer was separated and the aqueous layer extracted with additional methylene chloride (250 mL). The combined organic extracts were washed with water (250 mL), brine (250 mL), dried (Na$_2$SO$_4$) and concentrated in vacuo to a brown oil. Column chromatography on silica gel (1:9 ethyl acetate:methylene chloride) afforded a pale yellow foam (10.67 g, 79.0%). This was recrystallized from toluene to give 9.50 g of pure white crystals: mp 159°-161° C.; IR (KBr) 1757, 1676 cm$^{-1}$; $^1$H NMR (CDCl$_3$) delta 1.16 (t, J=7.5 Hz, 3H), 1.76 (d, J=5 Hz, 3H), 3.11 (s, 3H), 4.07 (q, J=7.5 Hz, 2H), 6.35 (q, J=5 Hz, 1H), 7.11 (m, 1H), 7.67-7.80 (m, 3H), 7.86-7.93 (m, 2H), 8.36 (m, 2H), 9.40 (br s, 1H); precise mass calcd for C$_{20}$H$_{21}$N$_3$O$_7$S m/e 447.1108, found 447.1164.

Anal. Calcd. for C$_{20}$H$_{21}$N$_3$O$_7$S: C, 53.68; H, 4.73; N, 9.39.

Found: C. 53.87; H, 4.77; N, 9.41.

EXAMPLE 17

4-[1-(Ethoxycarbonyloxy)ethoxy]-2-methyl-N-(5-methyl-3-isoxazolyl)-2H-1,2-benzothiazine-3-carboxamide 1,1-Dioxide By the method of Example 16, N-(5-methyl-3-isoxazolyl)-4-hydroxy-2-methyl-b 1,2-benzothiazine-3-carboxamide 1,1-dioxide (isoxicam; 0.5 g, 1.49 mmol) and alpha-chloroethyl ethyl carbonate (0.61 mL, 0.67 g, 4.46 mmol) were converted to chromatographed title product 0.61 g (91%) as a white foamy solid which was homogenous by TLC. Crystallization from isopropyl alcohol gave 0.52 g white crystalline solid: mp 158°–159° C.; IR (KBr) 1750, 1690 cm$^{-1}$; $^1$H NMR (CDCl$_3$) delta 1.20 (t, J=7.0 Hz, 3H), 1.75 (d, J=6.0 Hz, 3H), 2.47 (s, 3H), 3.08 (s, 3H), 4.10 (q, J=7.0 Hz, 2H), 6.34 (q, J=6.0 Hz, 1H) 6.83 (s, 1H), 7.77–7.97 (m, 4H), 9.45 (br s, 1H); precise mass calcd for C$_{19}$H$_{21}$N$_3$O$_8$S m/e 451.1059, found 451.1101.

Anal. Calcd. for C$_{19}$H$_{21}$N$_3$O$_8$S: C, 50.55; H, 4.69; N, 9.31.

Found: C, 50.21; H, 4.61; N, 9.15.

EXAMPLE 18

4-[1-(Butoxycarbonyloxy)ethoxy]-2-methyl-N-(2-pyridyl)-2H-1,2-benzothiazine-3-carboxamide 1,1-Dioxide By the procedure of Example 6, piroxicam (3.00 g, 9.1 mmol) and alpha-chloroethyl butyl carbonate (5.30 g, 29.3 mmol) were converted to title product, 600 mg yellow solid (1.3 mmol, 13.9%) which was recrystallized from isopropyl alcohol to give 325 mg white crystals: mp 132°–133° C.; IR (KBr) 1758, 1681 cm$^{-1}$; $^1$H NMR (CDCl$_3$) delta 0.87 (t, J=7 Hz, 3H), 1.18–1.35 (m, 2H), 1.42–1.58 (m, 2H), 1.76 (d, J=6 Hz, 3H), 3.11 (s, 3H), 4.01 (t, J=7 Hz, 2H), 6.35 (q, J=6 Hz, 1H), 7.05–7.15 (m, 1H), 7.65–7.82 (m, 3H), 7.82–7.95 (m, 2H), 8.30–8.40 (m, 2H), 9.39 (br s, 1H); precise mass calcd for C$_{22}$H$_{25}$N$_3$O$_7$S m/e 475.1413, found 475,1425.

Anal. Calcd. for C$_{22}$H$_{25}$N$_3$O$_7$S: C, 55.57; H, 5.30; N, 8.84.

Found: C, 55.41; H, 5.24; N, 8.64.

EXAMPLE 19

4-[1-(Octyloxycarbonyloxy)ethoxy]-2-methyl-N-(2-pyridyl)-2H-1,2-benzothiazine-3-carboxamide 1,1-Dioxide By the procedure of Example 11, piroxicam (3.00 g, 9.1 mmol) and alpha-chloroethyl octyl carbonate (3.25 g, 13.6 mmol) were converted to chromatographed title product isolated as a white solid, which gave 3.5 g white crystals from isopropyl alcohol (6.6 mmol, 72.7%): mp 93°–94° C.; IR (KBr) 1763, 1678 cm$^{-1}$; $^1$H NMR (CDCl$_3$) delta 0.88 (t, J=7 Hz, 3H), 1.10–1.39 (m, 10H), 1.53 (br t, 2H), 1.75 (d, J=6 Hz, 3H), 3.10 (s, 3H), 3.99 (t, J=7 Hz, 2H), 6.36 (q, J=6 Hz, 1H), 7.04–7.15 (m, 1H), 7.61–7.96 (m, 5H), 8.27–8.41 (m, 2H), 9.40 (br s, 1H); precise mass calcd for C$_{26}$H$_{33}$N$_3$O$_7$S m/e 531.2044, found 531.2100.

Anal. Calcd. for C$_{26}$H$_{33}$N$_3$O$_7$S: C, 58.74; H, 6.26; N, 7.90.

Found: C, 58.65; H, 6.24; N, 7.78.

EXAMPLE 20

4-[1-(Butyryloxy)ethoxy]-2-methyl-N-(2-pyridyl)-2H-1,2-benzothiazine-3-carboxamide 1,1-Dioxide By the procedure of Example 6, piroxicam (2.00 g, 6.0 mmol) and alpha-chloroethyl butyrate (2.75 g, 18.1 mmol) were converted to chromatographed title product, a white solid which was recrystallized from isopropyl alcohol to yield 1.07 g white crystals (2.41 mmol, 40.0%): mp 151°–152° C.; IR (KBr) 1755, 1678 cm$^{-1}$; $^1$H NMR (CDCl$_3$) delta 0.81 (t, J=7 Hz, 3H), 1.37–1.58 (m, 2H), 1.72 (d, J=6 Hz, 3H), 2.05–2.31 (m, 2H), 3.12 (s, 3H), 6.39 (q, J=6 Hz, 1H), 7.07–7.18 (m, 1H), 7.63–7.95 (m, 5H), 8.30–8.41 (m, 2H), 9.55 (br s, 1H); precise mass calcd for C$_{17}$H$_{16}$N$_3$O$_4$S (P—C$_4$H$_7$O$_2$) m/e 358.0865, found 358.0839.

Anal. Calcd. for C$_{21}$H$_{23}$N$_3$O$_6$S: C, 56.62; H, 5.20; N, 9.43.

Found: C, 56.62; H, 5.16; N, 9.43.

EXAMPLE 21

4-[1-(Acetyloxy)ethoxy]-2-methyl-N-(2-pyridyl)-2H-1,2-benzothiazine-3-carboxamide 1,1-Dioxide By the procedure of Example 5, piroxicam (2.00 g, 6.0 mmol) and alpha-chloroethyl acetate (2.22 g, 18.1 mmol) were converted to chromatographed title product, 1.17 g of yellow solid (2.8 mmol, 46.4%) which gave white crystals (1.08 g) upon crystallization from isopropyl alcohol: mp 161°–162° C.; IR (KBr) 1755, 1677 cm$^{-1}$; $^1$H NMR (CDCl$_3$) delta 1.72 (d, J=6 Hz, 3H), 1.95 (s, 3H), 3.13 (s, 3H), 6.39 (q, J=6 Hz, 1H), 7.07–7.18 (m, 1H), 7.65–7.96 (m, 5H), 8.30–8.42 (m, 2H), 9.52 (br s, 1H); precise mass calcd for C$_{17}$H$_{15}$N$_3$O$_5$S m/e (P$^+$—C$_2$H$_4$O) 373.0738, found 373.0678.

Anal. Calcd. for C$_{19}$H$_{19}$N$_3$O$_6$S: C, 54.67; H, 4.59; N, 10.07.

Found: C. 54.60; H, 4.54; N, 10.10.

EXAMPLE 22

4-[1-(Hexanoyloxy)ethoxy]-2-methyl-N-(2-pyridyl)-2H-1,2-benzothiazine-3-carboxamide 1,1-Dioxide By the procedure of Example 11, piroxicam (2.00 g, 6.0 mmol) and alpha-chloroethyl hexanoate (3.51 g, 19.6 mmol) were converted to chromatographed title product as yellow oil which was crystallized from toluene/hexane (1.21 g, 2.5 mmol, 42.1%): mp 62°–65° C.; IR (KBr) 1755, 1676 cm$^{-1}$; $^1$H NMR (CDCl$_3$) delta 0.81 (t, J=7 Hz, 3H), 1.00–1.30 (m 4H), 1.35–1.53 (m, 2H), 1.73 (d, J=6 Hz, 3H), 2.08–2.32 (m, 2H), 3.12 (s, 3H), 6.39 (q, J=6 Hz, 1H), 7.05–7.32 (m, 1H), 7.57–7.95 (m, 5H), 8.30–8.43 (m, 2H), 9.58 (br s, 1H): precise mass calcd for C$_{23}$H$_{28}$N$_3$O$_6$S m/e (P$^+$ +H) 474.1703, found 474.1645.

Anal. Calcd. for C$_{23}$H$_{27}$N$_3$O$_6$S: C, 58.34; H, 5.75; N, 8.87.

Found: C, 58.48; H, 5.79; N, 8.93.

EXAMPLE 23

4-[1-(Cyclopropylcarbonyloxy)ethoxy]-2-methyl-N-(2-pyridyl)-2H-1,2-benzothiazine-3-carboxamide 1,1-Dioxide By the procedure of Example 6, piroxicam (3.00 g, 9.1 mmol) and cyclopropanecarboxylic acid alpha-chloroethyl ester (4.03 g, 27.2 mmol) were converted to title product, 3.51 g white foam (7.0 mmol, 87.3%) which gave 1.90 g white crystals from toluene; mp 176°–177° C.; IR (KBr) 1735, 1680 cm$^{-1}$; $^1$H NMR (CDCl$_3$) delta 0.70–0.97 (m, 4H), 1.37–1.50 (m, 1H), 1.72 (d, J=6 Hz, 3H), 3.11 (s, 3H), 6.40 (q, J=6 Hz, 1H), 7.07–7.17 (m, 1H), 7.63.7.97 (m, 5H), 8.29–8.42 (m, 2H), 9.54 (br s, 1H); precise mass calcd for C$_{21}$H$_{22}$N$_3$O$_6$S m/e (P$^+$ +H) 444.1235, found 444.1013.

Anal. Calcd. for C$_{21}$H$_{21}$N$_3$O$_6$S: C, 56.88; H, 4.77; N, 9.48.

Found: C, 56.55; H, 4.70; N, 9.41.

EXAMPLE 24

4-[1-(Benzoyloxy)ethoxy]-2-methyl-N-(2-pyridyl)-2H-1,2-benzothiazine-3-carboxamide 1,1-Dioxide By the procedure of Example 6, piroxicam (3.00 g, 9.1 mmol) and alpha-chloroethyl benzoate (5.00 g, 27.0 mmol) were converted to chromatographed title product as a yellow oil which gave 3.41 g pure white crystals from isopropyl alcohol (7.1 mmol, 78.5%); mp 151°-152° C.; IR (KBr) 1748, 1681 cm$^{-1}$; $^1$H NMR (CDCl$_3$) delta 1.83 (d, J=6 Hz, 3H), 3.09 (s, 3H), 6.68 (q, J=6 Hz, 1H), 7.07-7.17 (m, 1H), 7.23-7.34 (m, 2H), 7.43-7.55 (m, 1H), 7.63-8.00 (m, 7H), 8.27-8.40 (m, 2H), 9.54 (br s, 1H); precise mass calcd for C$_{24}$H$_{21}$N$_3$O$_6$S m/e 479.1157, found 479.1062.

Anal. Calcd for C$_{24}$H$_{21}$N$_3$O$_6$S: C, 60.12; H, 4.41; N, 8.76.

Found: C, 60.10; H, 4.49; N, 8.83.

EXAMPLE 25

4-[1-(Octanoyloxy)ethoxy]-2-methyl-N-(2-pyridyl)-2H-1,2-benzothiazine-3-carboxamide 1,1-Dioxide To a round bottomed flask equipped with a reflux condenser and stirring bar were added piroxicam (3.00 g, 9.1 mmol), potassium carbonate (2.50 g, 18.1 mmol), alpha-chloroethyl octanoate (5.6 g, 27.0 mmol) and acetone (45 mL). The heterogenous reaction mixture was heated to reflux under a nitrogen atmosphere. After one hour sodium iodide (4.52 g, 30.2 mmol) was added and reflux continued an additional 72 hours. Chromatographed title product was isolated according to Example 5 as a white foam which oiled from toluene/hexane, but crystallized from the oil upon refrigeration. Collected were 2.19 g white crystals from two crops (4.4 mmol, 48.2%); mp 90°-91° C.; IR (KBr) 1766, 1675 cm$^{-1}$; $^1$H NMR (CDCl$_3$) delta 0.85 (t, J=7 Hz, 3H), 1.02-1.34 (m, 8H), 1.45 (d, br quintet, 2H), 1.73 (d, J=6 Hz, 3H), 2.08-2.33 (m, 2H), 3.12 (s, 3H), 6.40 (q, J=6 Hz, 1H), 7.06-7.17 (m, 1H), 7.63-7.95 (m, 5H), 8.30-8.42 (m, 2H), 9.56 (br s, 1H): precise mass calcd for C$_{23}$H$_{27}$N$_3$O$_5$S m/e (P$^+$—C$_2$H$_4$O) 457.1429, found 457.1700.

Anal. Calcd. for C$_{25}$H$_{31}$N$_3$O$_6$S: C, 59.86; H, 6.23; N, 8.38.

Found: C, 59.99; H, 6.11; N, 8.35.

EXAMPLE 26

4-[(2-Methoxycarbonyl-2-methylpropionyloxy)methoxy]-2-methyl-N-(2-pyridyl)-2H-1,2-benzothiazine-3-carboxamide 1,1-Dioxide To a dry round bottomed flask equipped with a reflux condenser and stirring bar were added piroxicam (1.50 g, 4.53 mmol), potassium carbonate (1.24 g, 8.98 mmol), iodomethyl methyl 2,2-dimethylmalonate (1.48 g, 5.17 mmol) and dry acetone (15 mL). The heterogenous reaction mixture was heated to reflux under a nitrogen atmosphere for 3 hours. Chromatographed title product was isolated according to the method of Example 5, 0.95 g (43.2%) light yellow solid which was recrystallized from toluene-hexane to give light yellow crystals: mp 112°-114° C.; IR (KBr) 1690, 1680 cm$^{-1}$; $^1$H NMR (CDCl$_3$) delta 1.28 (s, 6H), 3.11 (s, 3H), 3.62 (s, 3H), 5.76 (s, 2H), 7.08-7.18 (m, 1H), 7.70-7.88 (m, 4H), 7.89-7.99 (dd, J=8 Hz, J=4 Hz, 1H), 7.30-7.44 (m, 2H), 9.42 (s, 1H); precise mass calcd for C$_{22}$H$_{23}$N$_3$O$_6$S m/e 489.1205, found 489.1230.

Anal. Calcd for C$_{22}$H$_{23}$N$_3$O$_6$S: C, 53.99; H, 4.74; N, 8.58.

Found: C, 54.30; H, 4.86; N, 8.57.

EXAMPLE 27

4-(Octanoyloxy)methoxy-2-methyl-N-(2-pyridyl)-2H-1,2-benzothiazine-3-carboxamide 1,1-Dioxide To a round bottomed flask equipped with a reflux condenser and a stirring bar were added piroxicam (1.00 g, 3.0 mmol), potassium carbonate (840 mg, 6.0 mmol), chloromethyl octanoate (870 mg, 4.5 mmol) and acetone (15 mL). The heterogenous reaction mixture was heated to reflux under a nitrogen atmosphere. After 6 hours additional chloromethyl octanoate (250 mg, 0.75 mmol) and additional potassium carbonate (210 mg, 1.5 mmol) were added and reflux continued for an additional hour. Chromatographed title product was isolated, according to the method of Example 5, as a yellow foam which oiled from toluene/hexane, but crystallized from the oil upon refrigeration (690 mg white crystals, 1.4 mmol, 47%); mp 98°-99° C.; IR (KBr) 1766, 1683 cm$^{-1}$; $^1$H NMR (CDCl$_3$) delta 0.87 (t, J=8 Hz, 3H), 1.02-1.48 (m, 10H), 2.19 (t, J=6 Hz, 2H), 3.12 (s, 3H), 5.70 (s, 2H), 7.08-7.17 (m, 1H), 7.67-7.98 (m, 5H), 8.30-8.45 (m, 2H), 9.32 (br s, 1H); precise mass calcd for C$_{24}$H$_{30}$N$_3$O$_6$S m/e (P$^+$+H) 488.1859, found 488.1794.

Anal. Calcd. for C$_{24}$H$_{29}$N$_3$O$_6$S: C, 59.12; H, 6.00; N, 8.26.

Found: C, 59.51; H, 6.01; N, 8.72.

EXAMPLE 28

4-(Heptanoyloxy)methoxy-2-methyl-N-(2-pyridyl)-2H-1,2-benzothiazine-3-carboxamide 1,1-Dioxide By the procedure of Example 2, piroxicam (2.00 g, 6.0 mmol) and chloromethyl heptanoate (1.20 g, 66.4 mmol) were converted to chromatographed title product as a yellow oil. Attempted recrystallization from toluene/hexane produced an oil, but upon refrigeration the oil gave 1.01 g pure white crystals: (2.13 mmol, 35.3%); mp 98°-99° C.; IR (KBr) 1778, 1688 cm$^{-1}$; $^1$H NMR (CDCl$_3$) delta 0.85 (t, J=6 Hz, 3H), 1.05-1.47 (m, 8H), 2.20 (t, J=6 Hz, 2H), 3.13 (s, 3H), 5.69 (s, 2H), 7.06-7.17 (m, 1H), 7.68-8.00 (m, 5H), 8.30-8.42 (m, 2H), 9.33 (br s, 1H); precise mass calcd for C$_{23}$H$_{27}$N$_3$O$_6$S m/e 473.1620, found 473.1644.

Anal. Calcd. for C$_{23}$H$_{27}$N$_3$O$_6$S: C, 58.34; H, 5.75; N, 8.87.

Found: C, 58.39; H, 5.74; N, 8.99.

EXAMPLE 29

4-(Pivaloyloxy)methoxy-2-methyl-N-(2-pyridyl)-2H-1,2-benzothiazine-3-carboxamide 1,1-Dioxide By the procedure of Example 5, piroxicam (2.00 g, 6.0 mmol) and chloromethyl pivalate (2.61 mL, 2.73 g, 18.1 mmol) were converted to chromatographed title product as a white foam (1.78 g, 66.2%). Crystallization from toluene/hexane gave 1.56 g of pure white crystals: mp 132°-133° C.; IR (KBr) 1757, 1672 cm$^{-1}$; $^1$H NMR (CDCl$_3$) delta 1.03 (s, 9H), 3.12 (s, 3H), 5.74 (s, 2H), 7.08-7.17 (m, 1H), 7.68-7.87 (m, 4H), 7.92-7.99 (m, 1H), 8.30-8.43 (m, 2H), 9.48 (br s, 1H); precise mass calcd for C$_{21}$H$_{23}$N$_3$O$_6$S m/e 445.1313, found 445.1352.

Anal. Calcd. for C$_{21}$H$_{23}$N$_3$O$_6$S: C, 56.62; H, 5.20; N, 9.43.

Found: C, 56.63; H, 5.18; N, 9.47.

EXAMPLE 30

4-(Benzoyloxy)methoxy-2-methyl-N-(2-pyridyl)-2H-1,2-benzothiazine-3-carboxamide 1,1-Dioxide By the procedure of Example 6, piroxicam (3.33 g, 10.1 mmol) and chloromethyl benzoate (4.29 g, 25.0 mmol) were converted to chromatographed title product, 2.3 g (4.9 mmol), 48.9%) white foam which gave white crystals from isopropyl alcohol: mp 149°–150° C.; IR (KBr) 1745, 1687 cm$^{-1}$; $^1$H NMR (CDCl$_3$) delta 3.07 (s, 3H), 5.89 (s, 2H), 6.97–7.08 (m, 1H), 7.19–7.35 (m, 2H), 7.35–7.63 (m, 2H), 7.63–7.99 (m, 6H), 8.22–8.35 (m, 2H), 9.22 (br s, 1H); precise mass calcd for C$_{23}$H$_{19}$N$_3$O$_6$S m/e 465.1001, found 465.1051

Anal Calcd. for C$_{23}$H$_{19}$N$_3$O$_6$S: C, 59.35; H, 4.11; N, 9.03.

Found: C, 59.46; H, 4.10; N, 9.01

EXAMPLE 31

4-[(1-(Isobutyryloxy)ethoxy]-2-methyl-N-(2-pyridyl)-2H-1,2-benzothiazine-3-carboxamide 1,1-Dioxide By the procedure of Example 6, piroxicam (3.00 g, 9.1 mmol) and alpha-chloroethyl isobutyrate (4.10 g, 27.2 mmol) were converted to chromatographed title product, 3.50 g (7.9 mmol, 86.7%) white foam which was crystallized from isopropyl alcohol/hexane: mp 151°–153° C.; IR (KBr) 1751, 1680 cm$^{-1}$; $^1$H NMR (CDCl$_3$) delta 0.98 (d, J=1 Hz, 3H), 1.03 (d, J=1 Hz, 3H), 1.73 (d, J=6 Hz, 3H), 3.11 (s, 3H), 6.36 (q, J=6 Hz, 1H), 7.07–7.17 (m, 1H), 7.63–7.95 (m, 5H), 8.32–8.42 (m, 2H), 9.65 (br s, 1H); precise mass calcd for C$_{21}$H$_{23}$N$_3$O$_6$S m/e 445.1313, found 445.1240.

Anal. Calcd for C$_{21}$H$_{23}$N$_3$O$_6$S: C, 56.62; H, 5.20; N, 9.43.

Found: C, 56.19; H, 5.06; N, 9.37.

EXAMPLE 32

4-(Butyryloxy)methoxy-2-methyl-N-(2-pyridyl)-2H-1,2-benzothiazine-3-carboxamide 1,1-Dioxide To a round bottomed flask equipped with a reflux condenser and stirring bar were added piroxicam (1.00 g, 3.0 mmol), potassium carbonate (0.84 g, 6.1 mmol), chloromethyl butyrate (0.45 g, 3.3 mmol) and acetone (15 mL). The heterogenous reaction mixture was heated to reflux under a nitrogen atmosphere. After 24 hours the acetone was removed in vacuo leaving a yellow solid which was treated with water (100 mL) and methylene chloride (100 mL). The organic layer was separated and the aqueous layer extracted with additional methylene chloride (100 mL). The combined organic extracts were washed with water (100 mL), brine (100 mL), dried (Na$_2$SO$_4$) and concentrated in vacuo to a yellow oil. Column chromatography on silica gel (1:9 ethyl acetate/methylene chloride) afforded 260 mg of yellow oil which produced a white foam under vacuum (0.60 mmol, 20.2%). Attempted crystallization from toluene/hexane produced an oil, but with refrigeration the oil produced pure white crystals. Combined first and second crops yielded 86 mg white crystals; mp 202°–204° C.; IR (KBr) 1770, 1688 cm$^{-1}$; $^1$H NMR (CDCl$_3$) delta 0.79 (t, J=7 Hz, 3H), 1.35–1.53 (m, 2H), 2.18 (t, J=7 Hz, 2H), 3.12 (s, 3H), 5.70 (s, 2H), 7.05–7.18 (m, 1H), 7.65–7.88 (m, 4H), 7.88–7.99 (m, 1H), 8.28–8.42 (m, 2H), 9.32 (br s, 1H); precise mass calcd for C$_{20}$H$_{21}$N$_3$O$_6$S m/e 431.1151, found 431.1106.

Anal. Calcd. for C$_{20}$H$_{21}$N$_3$O$_6$S: C, 55.68; H, 4.91; N, 9.74.

Found: C, 55.28; H, 4.93; N, 9.75.

EXAMPLE 33

4[1-(Acetoxy)ethoxy]-2-methyl-N-(6-methyl-2-pyridyl)-2H-1,2-benzothiazine-3-carboxamide 1,1-dioxide To a round bottomed flask equipped with a reflux condenser and stirring bar were added N-(6-methyl-2-pyridyl)-4-hydroxy-2-methyl-2H-1,2-benzothiazine-3-carboxamide 1,1-dioxide (1.50 g, 4.34 mmol), potassium carbonate (1.20 g, 8.69 mmol), alpha-chloroethyl acetate (1.60 g, 13.03 mmol) and acetone (150 ml). The heterogenous reaction mixture was heated to reflux under a nitrogen atmosphere. After 24 hours, sodium iodide (2.60 g, 17.37 mmol) was added, and reflux continued an additional six hours. The acetone was removed in vacuo, leaving a yellow residue which was treated with water (300 ml) and methylene chloride (300 ml). The organic layer was separated and the aqueous layer extracted with additional methylene chloride (100 mL). The combined organic extracts were washed with water (300 mL), brine (200 mL), dried (Na$_2$SO$_4$) and concentrated in vacuo to a yellow solid. Column chromatography on silica (1:9 ethyl acetate:methylene chloride) afforded 1.64 g of a white solid (3.80 mmol, 87.3%), which crystallized from isopropyl alcohol to yield 1.50 g of title product as white crystals: mp 190°–191° C.; IR (KBr) 1770, 1682 cm$^{-1}$; $^1$H NMR (CDCl$_3$) delta 1.72 (d, J=6 Hz, 3H), 1.94 (s, 3H), 2.50 (s, 3H), 3.12 (s, 3H), 6.39 (q, J=6 Hz, 1H), 6.96 (d, J=6 Hz, 1H), 7.59–7.95 (m, 5H), 8.15 (d, J=6H, 1H), 9.39 (br s, 1H); precise mass calcd. for C$_{18}$H$_{17}$N$_3$O$_5$S m/e (P—C$_2$H$_4$O) 387.0894, found 387.0900.

Anal. Calcd. for C$_{20}$H$_{21}$N$_3$O$_6$S: C,55.68; H,4.91; N,9.74.

Found: C,55.51; H,4.91; N,9.70.

EXAMPLE 34

4[1-(Propionyloxy)ethoxy]-2-methyl-N(6-methyl-2-pyridyl)-2H-1,2-benzothiazine-3-carboxamide 1,1-dioxide To a round bottomed flask equipped with a reflux condenser and stirring bar were added 2-methyl-N-(6-methyl-2-pyridyl)-4-hydroxy-2H-1,2-benzothiazine-3-carboxamide 1,1-dioxide (1.50 g, 4.34 mmol), potassium carbonate (1.20 g, 8.69 mmol), alpha-chloroethyl propionate (1.78 g, 13.03 mmol) and acetone (150 ml). The heterogenous reaction mixture was heated to reflux under a nitrogen atmosphere. After 24 hours, sodium iodide (2.60 g, 17.4 mmol) was added, and reflux continued an additional six hours. The acetone was removed in vacuo, leaving a yellow residue which was treated with water (300 mL) and methylene chloride (300 mL). The organic layer was separated and the aqueous layer extracted with additional methylene chloride. The combined organic extracts were washed with water (300 mL), brine (200 mL), dried (Na$_2$SO$_4$) and concentrated in vacuo to a yellow solid. Column chromatography on silica (1:9 ethyl acetate:methylene chloride) afforded 1.65 g of a white solid (3.70 mmol, 85.3%), which crystallized from isopropyl alcohol to yield 1.55 g of a title product to white crystals: mp 174°–175° C.; IR (KBr) 1770, 1683 cm$^{-1}$; $^1$H NMR (CDCl$_3$) delta 0.97 (t, J=7 Hz, 3H), 1.71 (d, J=6 Hz, 3H), 2.10–2.38 (m, 2H), 2.49 (s, 3H), 3.11 (s, 3H), 6.39 (q, J=6 Hz, 1H), 6.96 (d, J=6

Hz, 1H), 7.59–7.96 (m, 5H), 8.13 (d, J=6 Hz, 1H), 9.45 (br s, 1H); precise mass calcd. for $C_{19}H_{19}N_3O_5S$ m/e (P—$C_2H_4O$) 401.1050, found 401.1025.

Anal. Calcd. for $C_{21}H_{23}N_3O_6S$: C,56.62; H,5.20; N,9.43.

Found: C,56.21; H,5.17; N,9.31.

PREPARATION 1 alpha-Chloroethyl Octyl Carbonate

To a stirring solution of dry n-octanol (6.42 g, 49.3 mmol) and pyridine (3.90 g, 49.3 mmol) in anhydrous ether (75 mL) was added at 0° C. alpha-chloroethyl chloroformate (prepared according to U.K. Pat. No. 1,426,717; 7.00 g, 49.3 mmol). The mixture was stirred vigorously for three hours at 25° C. then filtered. The filtrate was concentrated in vacuo and distilled at 102°–107° C. (2 mm) affording 8.1 g title product as a clear oil (34.2 mmol, 69.4%): $^1$H NMR (CDCl$_3$) delta 0.44–2.03 (m, 15H), 1.60 (d, J=6 Hz, 3H), 3.94 (t, J=7 Hz, 2H), 6.18 (q, J=6 Hz, 1H).

PREPARATION 2 alpha-Chloroethyl Hexyl Carbonate

By the procedure of Preparation 1, n-hexanol (5.04 g, 49.3 mmol) was converted to title product, distillation at 78°–81° C. (3 mm) affording 8.82 g as a clear oil (38.9 mmol, 79.0%): $^1$H NMR (CDCl$_3$) delta 0.50–2.18 (m, 11H), 1.81. (d, J=6 Hz, 3H), 4.15 (t, J=7 Hz, 2H), 6.36 (q, J=6 Hz, 1H)

PREPARATION 3 alpha-Chloroethyl Propyl Carbonate

By the procedure of Preparation 1, dry 1-propanol (2.95 g, 49.0 mmol) was converted to title product, distillation at 43°–45° C. (5 mm) affording 6.75 g (40.5 mmol, 82.7%) as a clear oil: $^1$H NMR (CDCl$_3$) delta 0.95 (t, J=7 Hz, 3H), 1.33–1.95 (m, 2H), 1.80 (d, J=6 Hz, 3H), 4.10 (t, J=7 Hz, 2H), 6.41 (q, J=6 Hz, 1H).

PREPARATION 4 alpha-Chloroethyl Decyl Carbonate

By the procedure of Preparation 1 n-decyl alcohol (7.75 g, 49.0 mmol) was converted to title product, distillation at at 110°–117° C. (1.5 mm) affording 10.5 g as a clear oil (39.7 mmol, 81.0%): $^1$H NMR (CDCl$_3$) delta 0.46–2.17 (br m, 19H), 1.85 (d, J=6 Hz, 3H), 4.20 (t, J=7 Hz), 6.42 (q, J=6 Hz, 1H).

PREPARATION 5 alpha-Chloroethyl Benzyl Carbonate

By the procedure of Preparation 1, benzyl alcohol (5.30 g, 49.0 mmol) was converted to title product, distillation at 111°–113° C. (3 mm) affording 8.3 g (38.7 mmol, 79.0%) as a clear oil: $^1$H NMR (CDCl$_3$) delta 1.75 (d, J=6 Hz, 3H), 5.17 (s, 2H), 6.41 (q, J=6 Hz, 1H), 6.80–7.28 (m, 5H).

PREPARATION 6 alpha-Chloroethyl Isopropyl Carbonate

By the procedure of Preparation 1, isopropyl alcohol (2.95 g, 49.0 mmol) was converted to title product, distillation at 57°–59° C. (10 mm) affording 5.04 g as a clear oil (30.3 mmol, 61.8%): $^1$H NMR (CDCl$_3$) delta 1.35 (d, J=7 Hz, 6H), 1.82 (d, J=6 Hz, 3H), 4.52–5.17 (m, 1H), 6.40 (q, J=6 Hz, 1H).

PREPARATION 7 alpha-Chloroethyl Cyclohexyl Carbonate

By the method of Preparation 1, cyclohexanol (4.90 g, 49.0 mmol) was converted to title product, distillation at 73°–77° C. (1 mm) affording 8.3 g as a clear oil (40.4 mmol, 82.4%): $^1$H NMR (CDCl$_3$) delta 0.80–2.30 (br m, 10H), 1.83 (d, J=6 Hz, 3H), 4.40–5.00 (br m, 1H), 6.42 (q, J=6 Hz, 1H).

PREPARATION 8 alpha-Chloroethyl Methyl Carbonate

By the procedure of Preparation 1, methanol (1.6 g, 50.0 mmol) was converted to title product, distillation at 35°–45° C. (11 mm) affording 3.5 g as a clear oil (25.3 mmol, 50.6%): $^1$NMR (CDCl$_3$) delta 1.90 (d, J=6 Hz, 3H), 3.95 (s, 3H), 6.48 (q, J=6 Hz, 1H).

PREPARATION 9 alpha-Chloroethyl Butyl Carbonate

By the procedure of Preparation 1, n-butanol (3.65 g, 49.3 mmol) was converted to title product, distillation at 60°–62° C. (5 mm) affording 5.2 g as a clear oil (28.8 mmol, 58.4%): $^1$H NMR (CDCl$_3$) delta 0.50–1.90 (m, 7H), 1.80 (d, J=6 Hz, 3H), 4.20 (t, J=7 Hz, 2H), 6.40 (q, J=6 Hz, 1H).

PREPARATION 10

Chloromethyl Butyrate

In a one liter beaker tetrabutylammonium hydrogen sulfate (38.54 g, 113.5 mmol) and sodium bicarbonate (9.53 g, 113.5 mmol) were combined with water (225 mL). When all forming had ceased, the solution was stirred and chloroform (675 mL) was added, followed by sodium butyrate (12.50 g, 113.5 mmol). The two phase system was stirred vigorously for 15 minutes, at which time the organic layer was separated, the aqueous layer extracted with chloroform (325 mL) and the combined organic extracts dried (Na$_2$SO$_4$) and evaporated in vacuo to a thick oil. To a stirring solution of the oil in acetone (650 mL) was rapidly added at room temperature a solution of iodochloromethane (20.0 g, 113.5 mmol) in acetone (25 mL). Stirring was continued 0.5 hour. The acetone was removed in vacuo to yield a white solid. Column chromatography on silica gel eluting with 9:1 methylene chloride:hexane and collecting the fractions containing the least polar spot by TLC (same eluant, R$_f$ 0.60, visualization by bromocresol green spray aided by heat) afforded chloromethyl butyrate as a pale yellow oil (3.00 g, 22.0 mmol, 19.4%): $^1$H NMR (CDCl$_3$) delta 0.80 (t, J=7 Hz, 23H), 1.45 (sextet, J=7 Hz, 2H), 2.16 (t, J=7 Hz, 2H), 5.77 (s, 2H).

PREPARATION 11

Chloromethyl Heptanoate

By the method of the preceding Preparation, sodium heptanoate (8.19 g, 53.8 mmol) was converted to crude title product. Column chromatography on silica gel eluting with 1:1 methylene chloride:hexane, and collecting the least polar spot by TLC (1:1 methylene chloride:hexane, R$_f$ 0.63, visualization by bromocresol green spray aided by heat) afforded chloromethyl heptanoate as a yellow tinted oil (1.20 g, 6.7 mmol, 12.5%): $^1$H NMR (CDCl$_3$) delta 0.65–2.00 (m, 11H), 2.40 (t, 2H), 5.78 (s, 2H).

PREPARATION 12

Chloromethyl Benzoate

By the procedure of Preparation 10, sodium benzoate (29.97 g, 208 mmol) was converted to crude title product, a thick oil which solidified upon standing at room temperature. TLC of this solid (3:2 hexane:methylene chloride, visualization by UV light) showed two contiguous spots ($R_f$ 0.65, 0.75) and a large baseline spot. The solid was treated with generous amounts of hexane and filtered. TLC of the filtrate showed only less polar products; TLC of the solid only baseline salts. The filtrate was concentrated in vacuo to a yellow oil and chromatographed on silica (3:2 hexane:methylene chloride). Fractions containing the least polar ($R_f$ 0.75) spot were combined and concentrated, affording 4.29 g (25.2 mmol, 12.0%) chloromethyl benzoate as a pale yellow oil: $^1$H NMR (CDCl$_3$) delta 5.95 (s, 2H), 7.15–7.61 (m, 3H), 7.85–8.18 (m, 2H).

PREPARATION 13

Chloromethyl Octanoate

By the procedure of Preparation 10, sodium octanoate (11.52 g, 69.3 mmol) was converted to crude title product as a yellow solid. Column chromatography on silica, eluting with 1:1 methylene chloride:hexane, and collecting fractions containing the least polar spot by TLC (same eluant, $R_f$ 0.61, visualization by bromocresol green spray aided by heat) afforded chloromethyl octanoate as a pale yellow oil (2.25 g, 11.7 mmol, 17.0%): $^1$H NMR (CDCl$_3$) delta 0.65–1.96 (m, 13H), 2.35 (t, J=7 Hz, 2H), 5.76 (s, 2H).

PREPARATION 14 alpha-Chloroethyl Acetate

To a three-necked round bottomed flask containing 1 g anhydrous zinc chloride was added freshly distilled acetyl chloride (21.33 mL, 23.55 g, 300 mmol). The cloudy, heterogenous mixture was stirred at room temperature under a nitrogen atmosphere for 15 minutes, then cooled to −15° C. Acetaldehyde (16.18 mL, 12.73 g, 289 mmol) was added at a rate such that the reaction temperature did not exceed 0° C. The orange solution was allowed to warm to room temperature then distilled at 27°–32° C. (17 mm Hg) to afford title product as a colorless oil (27.1 g, 221 mmol, 76.5%): $^1$H NMR (CDCl$_3$) delta 1.79 (d, J=7 Hz, 3H), 2.10 (s, 3H), 6.49 (q, J=7 Hz, 1H).

PREPARATION 15 alpha-Chloroethyl Benzoate

By the procedure of the preceding Preparation, freshly distilled benzoyl chloride (58.0 mL, 70.3 g, 500 mmole) was reacted with acetaldehyde (27.9 mL, 22.0 g, 500 mmol), added at a rate such that the reaction temperature did not exceed 5° C. during the addition. When the addition was complete, the orange solution was allowed to warm to room temperature, then treated with water (100 mL) and methylene chloride (100 mL). The pH was adjusted to 7.0 and the organic layer was isolated, washed with water (100 mL), brine (100 mL), dried (Na$_2$SO$_4$) and concentrated in vacuo to a dark brown oil (83.0 g). $^1$H NMR indicated less than 0.5% hexanoyl chloride in the product mixture. TLC (CH$_2$Cl$_2$) showed two UV active spots ($R_f$ 0.60, 0.65). A 10.0 g aliquot of the oil was chromatographed on silica gel (methylene chloride) affording 7.3 g of title product as the less polar ($R_f$ 0.65) component: $^1$H NMR (CDCl$_3$) 1.88 (d, J=6 Hz, 3H), 6.78 (q, J=6 Hz, 1H), 7.15–7.70 (m, 3H), 7.70–8.20 (m, 2H).

PREPARATION 16 alpha-Chloroethyl Propionate

By the procedure of Preparation 14, freshly distilled propionyl chloride (21.72 mL, 23.13 g, 250 mmol) was converted to title product. Distillation at 40°–45° C. (17 mm Hg) afforded 9.0 g as a colorless oil (65.9 mmol, 26.4%): $^1$H NMR (CDCl$_3$) delta 1.15 (t, J=7 Hz, 3H), 1.76 (d, J=6 Hz), 2.24 (q, J=7 Hz, 2H), 6.50 (q, J=6 Hz, 1H).

PREPARATION 17 alpha-Chloroethyl Cyclopropanecarboxylate

By the procedure of Preparation 15, freshly distilled cyclopropanecarboxylic acid chloride (20.70 g, 198 mmol) was converted, without chromatography, to title product as a pale green oil (20.38 g, 137 mmol, 69.3%): $^1$NMR (CDCl$_3$) delta 0.64–1.16 (m, 4H), 1.32–1.86 (m, 1H), 1.82 (d, J=6 Hz, 3H), 6.55 (q, J=6 Hz, 1H).

PREPARATION 18 alpha-Chloroethyl Isobutyrate

By the procedure of the preceding Preparation, freshly distilled isobutyryl chloride (30.08 g, 289 mmol) was converted to title product as a pale green oil (33.7 g, 224 mmol, 77.5%): $^1$H NMR (CDCl$_3$) delta 1.20 (d, J=7 Hz, 6H), 1.80 (d, J=6 Hz, 3H), 2.53 (quintet, J=7 Hz, 1H), 6.50 (q, J=6 Hz, 1H).

PREPARATION 19 alpha-Chloroethyl Hexanoate

By the procedure of Preparation 17, distilled hexanoyl chloride (35.1 mL, 24.9 g, 185 mmol) was converted to title product as a pale green oil (19.3 g, 126 mmol, 68.1%): $^1$NMR (CDCl$_3$) delta 0.80–2.20 (m, 11H), 1.76 (d, J=6 Hz, 3H), 2.36 (t, J=7 Hz, 2H) 6.58 (q, J=6 Hz, 1H).

PREPARATION 20 alpha-Chloroethyl Butyrate

By the procedure of Preparation 14, freshly distilled butyryl chloride (25.96 mL, 26.64 g, 250.0 mmol) was converted to title product. Distillation at 35°–45° C. (13 mm) afforded 15.0 g as a colorless oil (99.6 mmol, 39.8%): $^1$H NMR (CDCl$_3$) delta 0.93 (t, J=7 Hz, 3H), 1.16–2.00 (m, 2H), 1.75 (d, J=6 Hz, 3H), 2.30 (t, J=7 Hz, 3H), 6.50 (q, J=6 Hz, 1H).

PREPARATION 21 alpha-Chloroethyl Octanoate

By the procedure of Preparation 17, freshly distilled octanoyl chloride (43.6 mL, 41.48 g, 255 mmol) was converted to title product as a pale green oil (44.2 g, 214 mmol, 83.9%): $^1$H NMR (CDCl$_3$) delta 0.50–1.99 (m, 13H), 1.76 (d, J=6 Hz, 3H), 2.30 (t, J=7 Hz, 2H), 6.49 (q, J=6 Hz, 1H).

I claim:

1. A compound having the formula

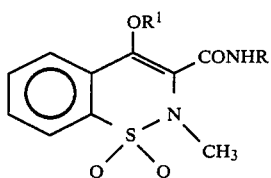 (I)

or

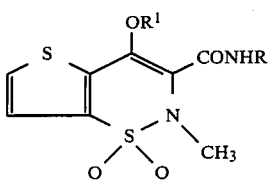 (II)

wherein R is

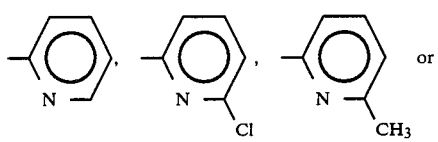 or

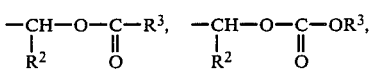 ;

and $R^1$ is

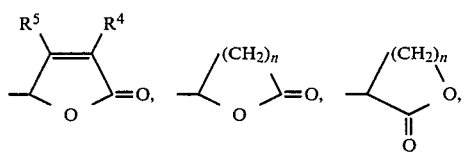

n is 2, 3 or 4;
$R^2$ is hydrogen, methyl or phenyl;
$R^4$ and $R^5$ are each independently hydrogen or methyl;
$R^3$ is $(C_1-C_{10})$alkyl, $(C_3-C_7)$cycloalkyl, phenyl or benzyl, each optionally substituted by $OR^6$ or $OCOR^6$, and
$R^6$ is $(C_1-C_3)$alkyl.

2. A compound of claim 1 having the formula (I) wherein R is

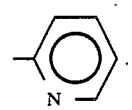

3. A compound of claim 2 wherein $R^1$ is

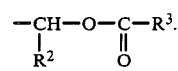

4. The compound of claim 3 wherein $R^2$ is methyl and $R^3$ is ethyl.

5. The compound of claim 3 wherein $R^2$ is methyl and $R^3$ is cyclopropyl.

6. The compound of claim 3 wherein $R^2$ is methyl and $R^3$ is phenyl.

7. The compound of claim 3 wherein $R^2$ is hydrogen and $R^3$ is 2-methyl-2-(methoxycarbonyl)ethyl.

8. A compound of claim 2 wherein $R^1$ is

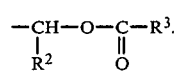

9. The compound of claim 8 wherein $R^2$ is methyl and $R^3$ is ethyl.

10. The compound of claim 8 wherein $R^2$ is methyl and $R^3$ is benzyl.

11. The compound of claim 8 wherein $R^2$ is methyl and $R^3$ is decyl.

12. The compound of claim 8 wherein $R^2$ is methyl and $R^3$ is cyclohexyl.

13. The compound of claim 2 wherein $R^1$ is

14. The compound of claim 2 wherein $R^1$ is

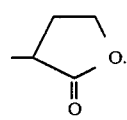

15. The compound of claim 2 wherein $R^1$ is

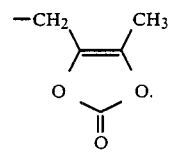

16. The compound of claim 2 wherein $R^1$ is

17. A compound of claim 1 having the formula (I) wherein R is

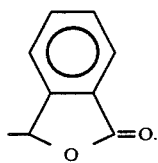

18. The compound of claim 17 wherein $R^1$ is $$-\underset{\underset{CH_3}{|}}{CH}-O-\overset{\overset{O}{\|}}{C}-O-C_2H_5.$$

19. A compound of claim 1 having the formula (I) wherein R is

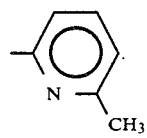

20. The compound of claim 19 wherein $R^1$ is $$-\underset{\underset{CH_3}{|}}{CH}-O-\overset{\overset{O}{\|}}{C}-O-C_2H_5.$$

21. The compound of claim 19 wherein $R^1$ is $$-\underset{\underset{CH_3}{|}}{CH}-O-\overset{\overset{O}{\|}}{C}-CH_3.$$

22. The compound of claim 19 wherein $R^1$ is $$-\underset{\underset{CH_3}{|}}{CH}-O-\overset{\overset{O}{\|}}{C}-C_2H_5.$$

23. A compound of claim 1 having the formula (II) wherein R is

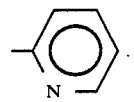

24. The compound of claim 23 wherein $R^1$ is $$-\underset{\underset{CH_3}{|}}{CH}-O-\overset{\overset{O}{\|}}{C}-O-C_2H_5.$$

25. A compound of claim 1 having the formula (I) wherein R is

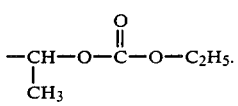

26. The compound of claim 25 wherein $R^1$ is $$-\underset{\underset{CH_3}{|}}{CH}-O-\overset{\overset{O}{\|}}{C}-O-C_2H_5.$$

27. An anti-inflammatory composition which comprises an anti-inflammatory amount of a compound of claim 1.

28. A method of treating inflammatory conditions in a mammal which comprises oral administration of an anti-inflammatory amount of a compound of claim 1.

* * * * *

UNITED STATES PATENT AND TRADEMARK OFFICE
CERTIFICATE OF CORRECTION

PATENT NO. : 4,551,452
DATED : November 5, 1985
INVENTOR(S) : Anthony Marfat

It is certified that error appears in the above-identified patent and that said Letters Patent is hereby corrected as shown below:

1. In the specification, at column 3, line 44, "$(I < Br < Cl)$" should be corrected to read --$(I > Br > Cl)$--.

2. In claim 8, the formula should be corrected to read:

$$-\overset{}{\underset{R^2}{-CH}}-O-\overset{}{\underset{O}{C}}-OR^3-.$$

Signed and Sealed this

Twenty-fourth Day of June 1986

[SEAL]

Attest:

DONALD J. QUIGG

Attesting Officer

Commissioner of Patents and Trademarks